(12) United States Patent
Page et al.

(10) Patent No.: US 7,514,676 B1
(45) Date of Patent: Apr. 7, 2009

(54) METHOD AND APPARATUS FOR SELECTIVE FILTERING OF IONS

(75) Inventors: Jason S. Page, Kennewick, WA (US);
Keqi Tang, Richland, WA (US);
Richard D. Smith, Richland, WA (US)

(73) Assignee: Battelle Memorial Insitute, Richland, WA (US)

( * ) Notice: Subject to any disclaimer, the term of this patent is extended or adjusted under 35 U.S.C. 154(b) by 204 days.

(21) Appl. No.: 11/251,529

(22) Filed: Sep. 30, 2005

(51) Int. Cl.
*B01D 59/44* (2006.01)
*H01J 49/00* (2006.01)

(52) U.S. Cl. .................. 250/288; 250/281; 250/282; 250/286; 250/287; 250/290; 250/291; 250/292; 250/396 R; 250/423 R (58) Field of Classification Search .......... 250/281, 250/282, 286, 287, 288, 292, 423 R, 396 R, 250/290, 291
See application file for complete search history.

(56) References Cited

U.S. PATENT DOCUMENTS

| | | | | |
|---|---|---|---|---|
| 5,514,868 | A * | 5/1996 | Dixon | 250/282 |
| 6,107,628 | A * | 8/2000 | Smith et al. | 250/292 |
| 6,124,592 | A * | 9/2000 | Spangler | 250/287 |
| 6,903,331 | B2 * | 6/2005 | Bateman et al. | 250/287 |
| 7,368,709 | B2 * | 5/2008 | Guevremont et al. | 250/282 |

OTHER PUBLICATIONS

Page, et al., Variable low-mass filtering using an electrodynamic ion funnel, J. Mass Spectrom 2005, 40, pp. 1215-1222.

* cited by examiner

*Primary Examiner*—Jack I Berman
*Assistant Examiner*—Meenakshi S Sahu
(74) *Attorney, Agent, or Firm*—James D. Matheson (57) ABSTRACT

An adjustable, low mass-to-charge (m/z) filter is disclosed employing electrospray ionization to block ions associated with unwanted low m/z species from entering the mass spectrometer and contributing their space charge to down-stream ion accumulation steps. The low-mass filter is made by using an adjustable potential energy barrier from the conductance limiting terminal electrode of an electrodynamic ion funnel, which prohibits species with higher ion mobilities from being transmitted. The filter provides a linear voltage adjustment of low-mass filtering from m/z values from about 50 to about 500. Mass filtering above m/z 500 can also be performed; however, higher m/z species are attenuated. The mass filter was evaluated with a liquid chromatography-mass spectrometry analysis of an albumin tryptic digest and resulted in the ability to block low-mass, "background" ions which account for 40-70% of the total ion current from the ESI source during peak elution.

15 Claims, 9 Drawing Sheets

METHOD AND APPARATUS FOR SELECTIVE FILTERING OF IONS

This invention was made with Government support under Contract DE-AC05-76RLO1830 awarded by the U.S. Department of Energy. The Government has certain rights in the invention.

FIELD OF THE INVENTION

The present invention relates generally to a method for selective filtering of ions. More particularly, the invention relates to a method for selective filtering of low-m/z ions that is used in conjunction with, e.g., an electrodynamic ion funnel conductance limit, or terminating, electrode. The invention finds application in, e.g., analytical instruments and associated systems including, but not limited to, e.g., mass-selective instruments and components, coupled stages, and/or ionization sources and components including, but not limited to, e.g., MS, IMS/MS, FAIMS/MS, GC-MS, LC-MS, ESI-MS, and the like.

BACKGROUND OF THE INVENTION

Electrospray ionization (ESI) mass spectrometry (MS), or ESI-MS, has become a vital tool in biological research. Central to ESI-MS is the manipulation, transmission, and increasingly the trapping of ion populations. In a population of ions, electric fields of the ions influence each other and the collective effect is known as space charge. The detrimental effects of excessive space charge on instrumental performance are well known in the art. For example, like-charged ions repel each other, and the electric field of an ion cloud distorts the electric fields from the elements, optics, and mass analyzer of the mass spectrometer. Further, space charge reduces the mass measurement accuracy in various instruments, including, e.g., Fourier transform ion cyclotron resonance (FTICR) MS. Similarly, 3-D ion traps suffer from detrimental effects from excessive space charge which leads to shifts in secular frequencies, changes in optimal excitation amplitudes, and plasma effects. Space charge can also cause radial stratification of ions and unwanted fragmentation in accumulation quadrupoles or multipoles in general. Various strategies and techniques have been employed in an attempt to reduce the influence of space charge, including, e.g., data-dependent corrections and calibrations and automated methods which regulate and decrease the variation of ion populations in a mass analyzer. However, data-dependent corrections and calibrations do not reduce or eliminate space-charge effects. Further, such approaches are limited in that they cannot distinguish ions of interest from those that constitute background ions.

Accordingly, there remains a need for methods and devices that significantly reduce and/or eliminate space-charge effects in analytical instruments and related components or systems thereby improving analysis results.

SUMMARY OF THE INVENTION

In one aspect, the invention is a low m/z filtering apparatus, comprising a filtering plate or electrode positioned at an exit point or a terminating aperture of an ion funnel, wherein the filtering plate is biased in conjunction with a power supply for applying adjustable DC voltage(s) to the filtering plate or electrode without affecting voltages of the funnel. Voltage(s) when applied to the filtering plate or electrode generates a barrier potential prohibiting ions introduced to the funnel from exiting the funnel having a kinetic (m/z) energy lower (i.e., lower mass-to-charge ratio) than the barrier potential thereby filtering the lower m/z ions.

In another aspect, the invention is a method for reducing and/or eliminating space charge contributed by low m/z ion species comprising: providing an ion funnel including a filtering plate or electrode coupled thereto at an exit point for ions traveling therethrough, wherein the filtering plate or electrode is isolated from the DC and/or RF voltages of the funnel and biased in conjunction with an independent DC power supply for applying DC voltages to the filtering plate or electrode without affecting voltages of the ion funnel. Voltages when applied to the filtering plate or electrode generate a barrier potential that prohibits ions introduced to the funnel having a lower kinetic energy (lower m/z) than the barrier potential from exiting the ion funnel thereby filtering lower m/z ions.

In another aspect, the invention is a method for filtering low m/z ions, comprising: providing a filtering plate or electrode in an ion funnel at the exit point for ions traveling through the funnel, wherein the filtering plate or electrode is biased in conjunction with a power supply operable for applying adjustable DC voltage(s) to the filtering plate or electrode without affecting voltages of the funnel; and wherein the voltage(s) when applied to the filtering plate or electrode generate a barrier potential prohibiting ions introduced to the funnel from exiting the funnel having a kinetic energy lower (i.e., lower mass-to-charge ratio) than the barrier potential thereby filtering the lower m/z ions from an ion stream exiting the funnel thereby reducing or eliminating space charge effects contributed to ion current by the lower m/z ions.

In an embodiment, the operating pressure for the filtering member is in the range from about 1 Torr to about 30 Torr, or in the range from about 1 Torr to about 3 Torr.

In another embodiment, the voltage of the filtering member is dynamically adjustable providing a linear voltage adjustment for effecting ion separation of an analysis instrument or analysis system in real-time.

In another embodiment, filtering comprises selection of m/z values for ions in the range from about m/z of 50 to about m/z of 500.

In another embodiment, filtering comprises selection of m/z values for ions above an m/z of about 500 in conjunction with enhanced voltage gain to compensate for loss of signal or signal attenuation.

In another embodiment, the filtering apparatus is sequentially coupled to one or more devices or systems for gas-phase ion separation and analysis selected from ion mobility spectrometry (IMS), field asymmetric waveform ion mobility spectrometry (FAIMS), mass spectrometry (MS), tandem MS, multiple MS stages of any kind, gas chromatography (GC), LC-MS, photoelectron spectroscopy, photodissociation spectroscopy, ionization sources, ESI-MS, or combinations thereof.

In another embodiment, the filtering apparatus is coupled on-line or off-line to at least one apparatus for separations and analysis of substances in solid or liquid phases selected from the group consisting of liquid chromatography (LC), normal phase LC, reversed phase LC, strong-cation exchange LC, supercritical fluid chromatography, capillary electrophoresis, capillary isoelectric focusing, gel separations in one or more dimensions, SDS-PAGE, 2-D gel, or combinations thereof.

In another embodiment, ions are biological or macro-molecular ions selected from the group consisting of proteins, protein complexes, peptides, polypeptides, oligonucleotides, DNA, RNA, polymers, oligosaccharides, dendrimers, fragments thereof, or combinations thereof.

The apparatus and method of the invention can be used alone or in conjunction with other established devices and methods that lessen detrimental effects associated with excessive space charge. Central to this technique is the exploitation of kinetic energy distributions of low m/z ion species.

DETAILED DESCRIPTION

While the present disclosure is exemplified by specific embodiments, it should be understood that the invention is not limited thereto, and variations in form and detail may be made without departing from the spirit and scope of the invention. All such modifications as would be envisioned by those of skill in the art are hereby incorporated.

The present invention relates generally to method and apparatus for selective ion filtering. More particularly, the invention relates to a method and apparatus for filtering of low-m/z ions in conjunction with use of an electrodynamic ion funnel. The mass filtering approach described herein provides a simple means for reducing space-charge. The approach selectively eliminates undesired ions, lowering the ion population and unwanted space-charge effects associated with the same thereby enhancing instrument performance.

In one embodiment, the invention employs an ionization source, an ion funnel, and the low-mass filter in combination providing a simple means to reduce the amount of space charge in the receiving instrument by blocking (filtering) ions in a defined, lower-mass region. The combination is effective for at least the following reasons. First, most of the background ion current is typically made up of low-mass species that are often solvent or matrix derived. Secondly, many MS applications, e.g., proteomics, do not utilize low m/z species. In peptide and protein, analyses (e.g., LC-MS), the mass range of interest is typically higher than an m/z of about 200. Thus, the low m/z filter can be employed without adversely affecting the analysis. Additionally, the ability to easily and dynamically set the maximum m/z cut-off of the filter allows for the tailoring of the device to better match the m/z range requirements of various samples. Further, the use of variable low-mass filtering in an electrodynamic ion funnel can be used alone or in conjunction with other space charge limiting techniques (such as automated gain control) to increase mass spectrometer performance and provide improved data quality.

Figure 1:
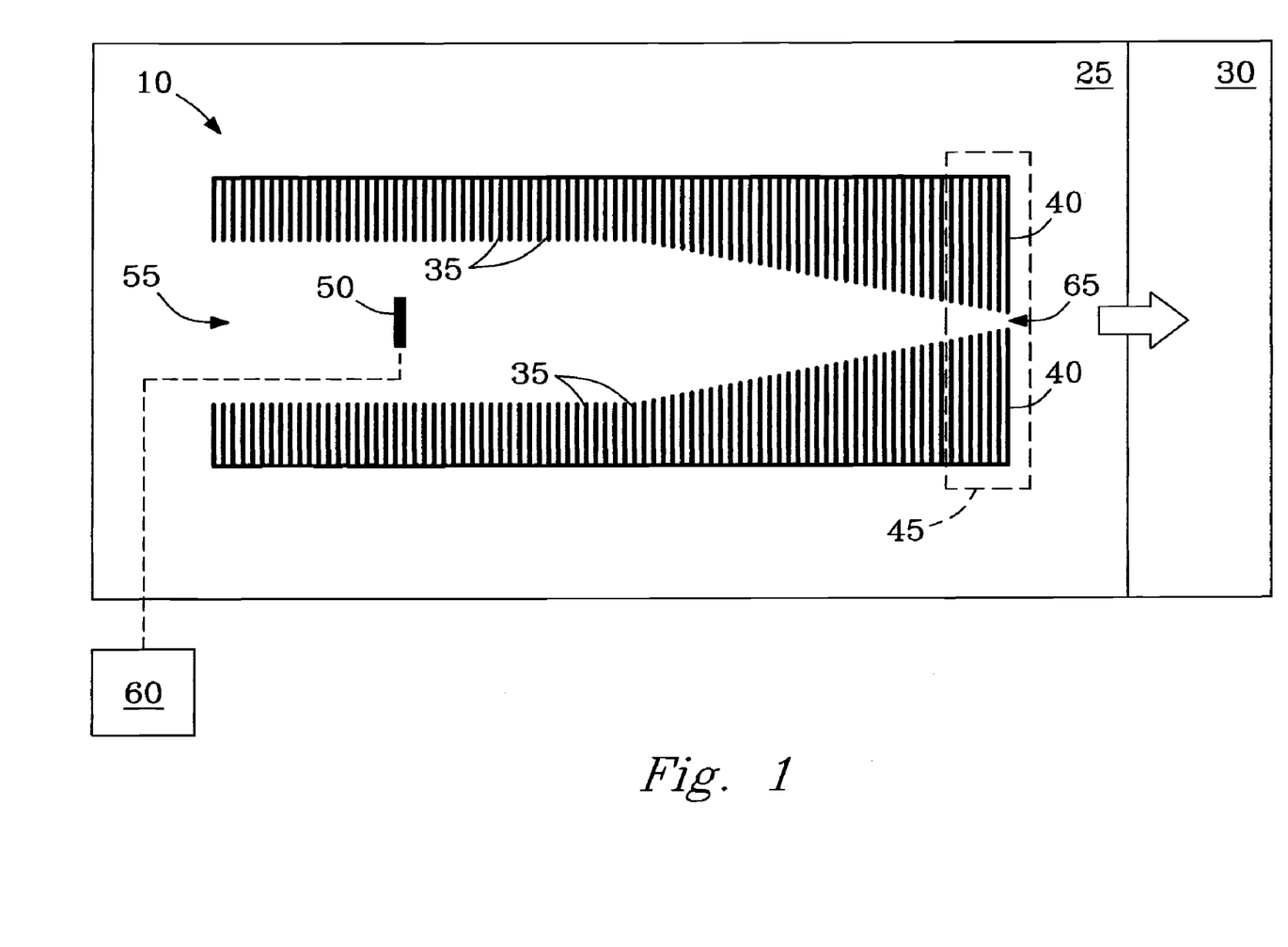
FIG. 1 is a cross-sectional illustration of an ion funnel that includes a conductance limit electrode as a filter plate and a jet disrupter electrode.

FIG. 1 illustrates a longitudinal, cross-sectional view of an ion funnel 10 configured with a conductance limiting or terminating electrode 40, that, in conjunction with the preferred embodiment of the method of the invention, can act as a mass (m/z) filter (hereafter called filter plate 40), as described and demonstrated hereafter. Ion funnel 10 is a special ion guide tapered to improve transmission efficiency of ions in the interface region (not shown) between an ionization source 25, e.g., an Electrospray Ionization Source (ESI), and a mass-selective instrument or analyzer 30, e.g., mass spectrometer 30. In the figure, ion funnel 10 comprises a stack of (e.g., 100) ring electrodes or plates 35, but is not limited thereto. Electrode plates 35 begin to exhibit sequentially decreasing aperture diameters at about the midpoint of the stack, culminating in a conductance limit (smallest aperture) electrode 40 positioned in rear section 45 of funnel 10. Funnel 10 operates in conjunction with a superimposed radio frequency (RF) voltage and a DC gradient that spans the length of funnel 10. Electronics that co-apply RF and DC potentials and/or gradients, including, but not limited to, e.g., a uniform ladder of DC voltages in various modes to a series of electrodes is detailed, e.g., in Smith et al. (U.S. Pat. No. 6,107,628) which is incorporated herein by reference. All electrode configurations and processes as will be selected by those skilled in the art in view of the disclosure are incorporated herein by reference. No limitations are intended.

In the figure, ion funnel 10 is includes a jet disrupter 50, which is, e.g., a 6.5 mm diameter metal disk located about one inch from the funnel 10 inlet 55 electrically isolated from voltages of the ion funnel 10 and controlled by an independent DC power supply 60. Jet disrupter 50 disperses the gas jet exiting the heated capillary of ion funnel 10, reducing the gas load to a subsequent stage and prohibits neutrals from entering the mass spectrometer.

Mass filter 40 is easily implemented, independent of the type of instrument, and is contained solely within ionization source 25 thereby eliminating the need to change any elements or potentials in the mass spectrometer. The MS analyzer employed in conjunction with the invention may be of any type, including but not limited to sector, quadrupole, time-of-flight (ToF), quadrupole trap, orbitrap, Fourier-transform ion cyclotron resonance (FTICR), or combinations thereof. In addition, the MS analyzer can be coupled to other instruments, devices, tools, software, reagents, and/or consumables as will be understood and/or contemplated by those of skill in the art, without limitation.

When a DC voltage (potential) is applied to filter plate 40 or the conductance limiting electrode 40 of ion funnel 10, an energy barrier (electric field) is generated, filtering (e.g., blocking) low mass (m/z) ions from exiting the ionization source 25 through exit aperture 65. The barrier potential generated as a function of applied voltage to the upper limit of mass filter 40 is approximately linear. Thus, voltage required to provide a desired m/z filter 40 is easily calculated. The ability to change potential on filter plate 40 to provide a desired mass filter range allows for quick adjustments to the instrument based on sample properties, providing for dynamic low-m/z filtering in an automated process. Height of the barrier or potential can be easily controlled by adjusting the voltage applied to filter plate 40. The energy barrier potential exploits the ion mobility and the characteristic kinetic energy spread of lower-m/z source ions allowing selection of a particular mass (m/z) cut-off (mass filter) for the filter plate 40.

When a positive DC potential is applied to filter plate 40 of ion funnel 10, ion velocity is defined by the balance of the drag force from the gas flow and the force from the applied electric field. The free ion motion model that assumes conservation of the sum of ion kinetic and potential energies is not applicable under the conditions of a high buffer gas pressure. Instead, one can apply a drift ion motion model, e.g., as used in ion mobility studies, where ion drift velocity ($V_{drift}$) is defined by equation [1]:

$$V_{drift} = KE \quad [1]$$

where $V_{drift}$ is the ion drift velocity, K is the mobility coefficient, and E is the DC electric field. In order to pass the DC electric field barrier generated at filter plate 40, the drift velocity of the ions should be smaller than the gas flow velocity. The mobility coefficient (K) can be further expressed via the collision cross section (a), as defined by equation [2]:

$$K = \frac{3ze}{16n\sigma}\left(\frac{2\pi}{m_r k_b T}\right)^{\frac{1}{2}} \quad [2]$$

where "n" is the buffer gas number density, "$k_b$" is the Boltzmann constant, "T" is the temperature, "ze" is the ion charge, and "$m_r$" is the reduced mass of the buffer gas and ion.

The linear dependence of the low m/z cut off as a function of the applied filter plate 40 voltage (described in reference to FIG. 4c herein) can be attributed to the mobility dependence on the ion size. Equation [2] shows that ion drift velocity is inversely proportional to the ion cross section (a). In a linear approximation, the cross section (σ) can be roughly evaluated via the ion mass (m), where, in equation [3]:

$$\sigma(m) \sim (\sigma_0 + c_1 m) \quad [3]$$

where $\sigma_0$ is the initial cross section, $c_1$ is a first order approximation constant, and m is the ion mass. This correlation is revealed in ion mobility/MS experiments that show ion drift times increasing linearly with m/z within a specific charge state "z". For example, substituting σ(m) of equation [3] into equation [2], one obtains a linear dependence for low-mass (m/z) cut off as a function of the DC field at exit 65, which in turn is proportional to the DC offset. A linear fit to experimental data (e.g., as shown in FIG. 4c) yields the relationship shown in equation [4]:

$$\sigma = 104 \text{ Å}^2 + 0.09*(m/z) \quad [4]$$

The term σ=104 Å$^2$ can be interpreted as the cross section due to long-term, e.g. ion-dipole, interactions. The second term, 0.09*(m/z), represents the hard-core cross section that is proportional to ion size. The model of gas flow-electric field competition gives the correct order of magnitude estimation for the behavior observed experimentally. Ion species blocked by the DC field at exit 65 are accumulated in the effective potential well at exit 65, wherein low m/z instability (elimination) is caused by radial ejection due to ion cloud expansion.

Figure 2A:
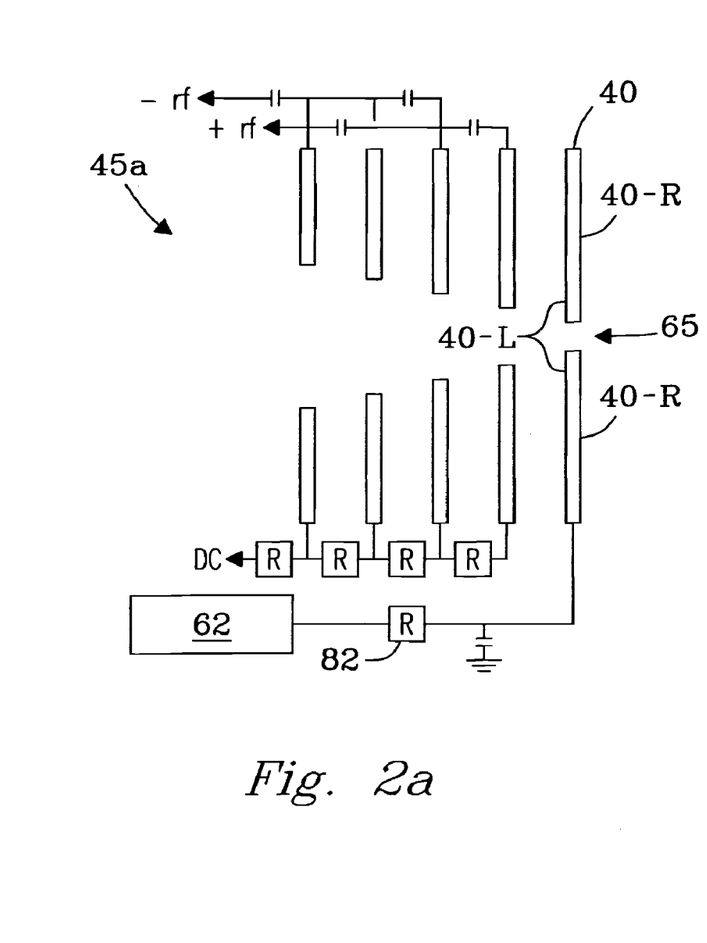
FIGS. 2a-2b illustrate configurations for low-m/z filtering in conjunction with use of an ion funnel, according to two embodiments of the invention.
Figure 2B:
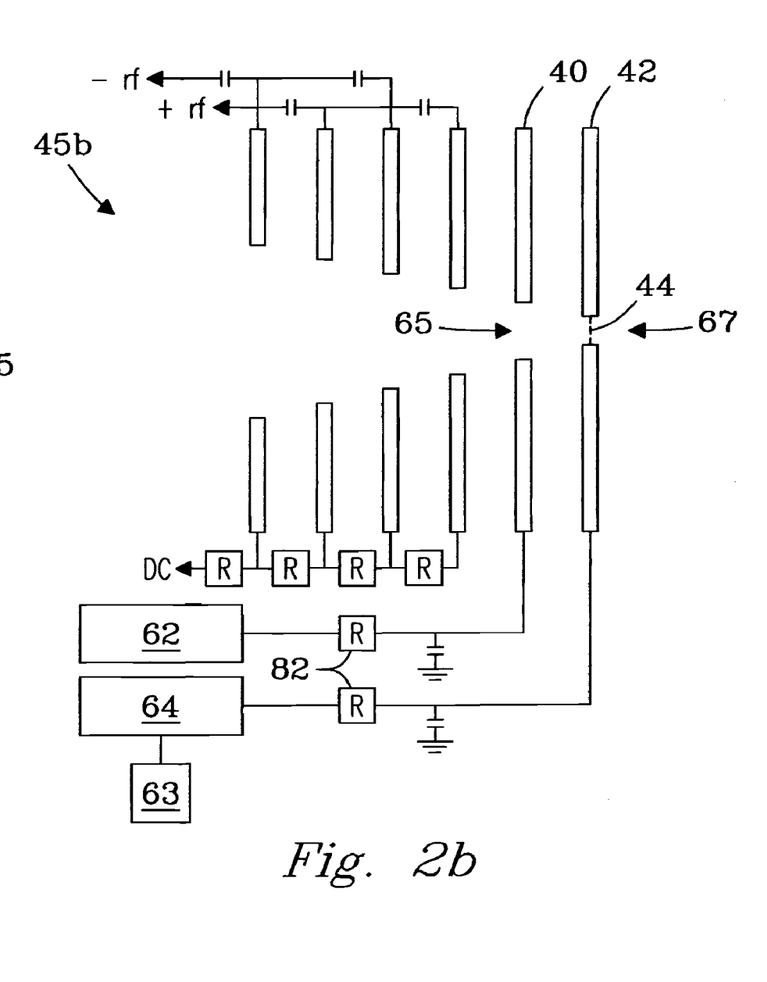

FIGS. 2a-2b illustrate two configurations for rear section 45 (45a and 45b) of ion funnel 10, according to two embodiments of the invention. FIG. 2a illustrates a first configuration for rear section 45 (i.e., 45a) of ion funnel 10 for effecting low-m/z filtering, showing a more detailed view of filtering plate 40. Filter plate 40 has a conductance limiting aperture 65 electrically isolated from the RF and DC gradient of funnel 10. As described herein, a voltage applied to filter plate 40 produces an energy barrier, turning plate 40 into a low-mass filter 40. Filter 40 is biased by an independent DC power supply 62 with a low-pass electrical filter 82, which is a simple RC circuit made with, e.g., a 240 kΩ resistor and natural capacitance of the co-axial cable coupled to the ground of power supply 62. Low-pass electrical filter 82 removes a majority of induced current generated by the RF of funnel 10. FIG. 2b illustrates a second configuration for rear section 45 (i.e., 45b) that permits detection and measurement of ion currents after filter 40. In the figure, a second DC-only electrode 42 is positioned in ion funnel 10 immediately after mass filter 40. An 83 lines per inch copper mesh 44 (Buckbee-Mears, St. Paul, Minn., USA) is placed across the 2 mm diameter exit aperture 67 of second plate 42 by machining an 8 mm diameter, 0.25 mm deep counter bore hole 67 at the center of plate 42 and adhering mesh 44 with a conductive, silver epoxy (ITW Chemtronics, Kennesaw, Ga.). In addition, low-pass electrical filter 82 is used to remove induced current caused by RF of funnel 10. Mesh plate 44 may be biased with a DC power supply 63 by "floating" the ground of picoammeter 64 (e.g., a Keithley Model 6485, Cleveland, Ohio) used to detect ion current impacting mesh 44.

In a typical operation, ion funnel 10 is operated, e.g., by applying an RF of 500 kHz at 90 V peak-to-peak ($V_{p-p}$), but is not limited thereto. At the stated RF value, DC voltage applied to ion funnel 10 generates a constant gradient of about 200 V at the inlet 55 down to 5 V at the outlet 65 or 67, but again is not limited thereto. In the instant operation, pressure in funnel 10 is about 1.9 Torr, but is not limited thereto.

The following examples are intended to promote a further understanding of the present invention.

EXAMPLES

Example 1 describes tests showing ability of the conductance limiting electrode to perform selective low-mass filtering as a low m/z filter. Example 2 describes tests relating m/z cut-off of filter 40 to potential applied to filter 40 necessary to achieve filtering of low m/z ions. Example 3 describes DC voltage distribution effects observed in the region near the aperture of filter plate 40 as a function of radial distance at an applied filter voltage of 15 V. Example 4 details effects associated ion funnel RF voltages on attenuation of higher-massed peaks above m/z 500 when using mass filter 40. Example 5 details use and evaluation of the low-mass filter 40 for a liquid chromatography-mass spectrometry (LC-MS) analysis of a Bovine Serum Albumin (BSA) tryptic digest.

Example 1

Example 1 describes tests showing ability of the conductance limiting electrode 40 of ion funnel 10 to perform selective low-mass filtering, e.g., as a low m/z filter 40.

Ability of conductance limiting electrode 40 of ion funnel 10 to perform selective low-mass filtering was tested on a single quadrupole mass spectrometer (e.g., model 1100 quadrupole MS, Agilent, Palo Alto, Calif., USA) modified with an ESI/ion funnel source. The ESI/ion funnel configuration described in reference to FIG. 2b was employed. Ion funnel 10 was operated by applying an RF voltage of 500 kHz at 90 V peak-to-peak (90 $V_{p-p}$), but was not limited thereto. DC voltage applied to funnel plates 35 of ion funnel 10 yielded a constant gradient of 200 V at inlet 55 down to 5 V at exit aperture 65 of ion funnel 10. Pressure in funnel 10 was 1.9 Torr. ESI emitters were made by pulling sections of 100-μm i.d./200-μm o.d. fused silica capillary (Polymicro Technologies, Phoenix, Ariz., USA) either by hand with a butane torch or with a Model 2000 capillary puller (Sutter Instrument Company, Novato, Calif., USA). For infusion experiments, the ESI emitter was connected to a transfer capillary and a 25 mL syringe (Hamilton, Las Vegas, Nev., USA) by a stainless steel union, which also served as the connection point for the ESI voltage. Solutions were infused at a 0.3 μL/min flow rate from a Harvard Apparatus Model 22 syringe pump (Holliston, Mass., USA). Voltages from 1.4 kV to 1.5 kV were applied to the ESI emitter via a Burtan high voltage power supply (e.g., Model 205B-03R, Hicksville, N.Y.). Terminal RF/DC plate 40 of funnel 10 was set to 5 V DC and the energy barrier was generated by biasing filter plate 40 to voltages above this value. An Agilent MS calibration solution (product code number G2421A, Palo Alto, Calif., USA) containing 7 fluorinated compounds producing singly charged ions in the ESI source was infused and electrosprayed into mass spectrometer 30. Mass spectra were acquired as the voltage to filter plate 40 was incremented. Mass spectra were acquired in positive ESI mode with a m/z step size of 0.1.

Figure 3A:
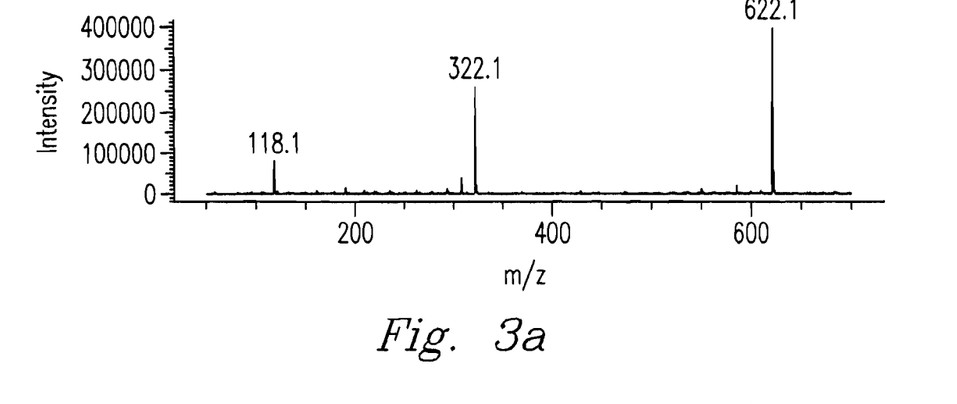
FIGS. 3a-3c present mass spectra of a calibration solution taken in conjunction with an ion funnel filter plate at 8V, 13.6 V, and 17.6 V, respectively.
Figure 3B:
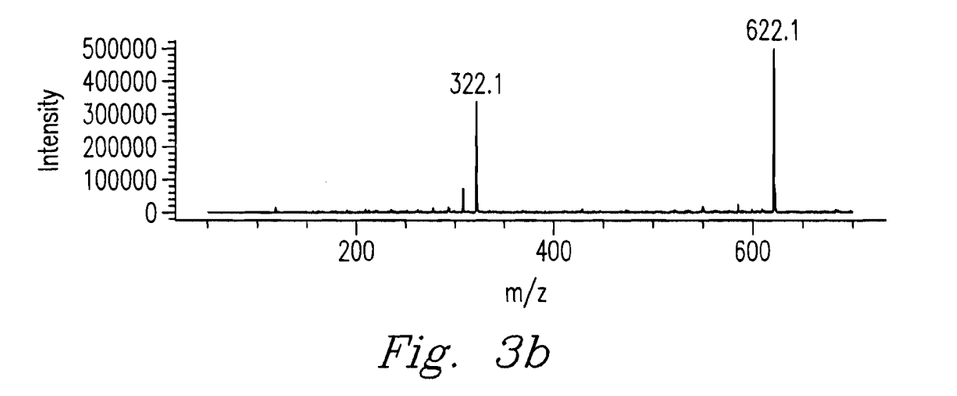
Figure 3C:
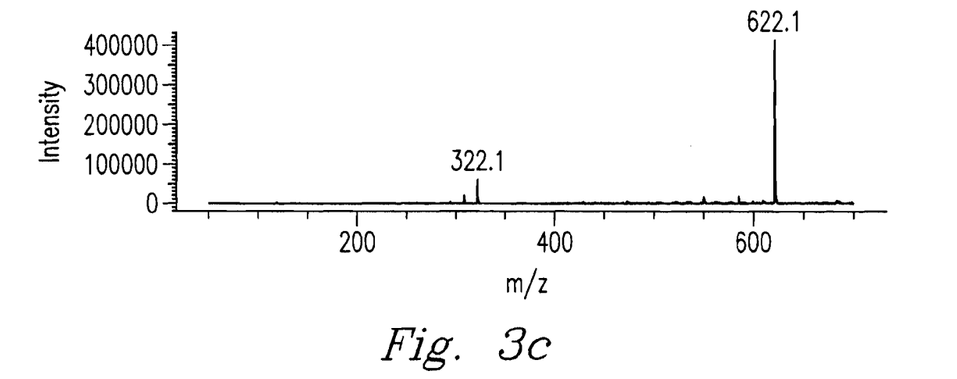

FIGS. 3a-3c present mass spectra from three representative MS analyses of the MS calibration solution at three different voltage settings applied to low-m/z filter 40 of ion funnel 10, i.e., 8 volts, 13.6 volts, and 17.6 volts, respectively. FIG. 3a shows that when voltage to filter plate 40 was set to 8 V, the barrier potential was too low to effectively block any ions from entering the quadrupole of the mass spectrometer. FIG. 3b presents the mass spectrum acquired using a filter plate 40 voltage of 13.6 V, showing the increase of 6 volts was sufficient to block most of the m/z 118.1 peak. FIG. 3c presents the mass spectrum acquired using a filter plate 40 voltage of 17.6 V. At 17.6 V, the voltage increased the effective range of low-mass filtering achieved by filter plate 40. A majority of the m/z 322.1 calibration peak was blocked without affecting the m/z 622.1 peak. Results show filter plate 40 provides a simple low-mass filter, generated by adding a barrier potential to exit aperture 65 of ion funnel 10.

Example 2

Example 2 describes tests relating m/z cut-off of filter plate 40 to the potential applied to filter plate 40 necessary to achieve filtering of low m/z ions.

A solvent mixture was prepared by combining methanol (Fisher Scientific, Pittsburgh, Pa., USA) and water (Nanopure Infinity Purification system, Barnstead, Dubuque, Iowa, USA) in a 50:50 ratio by volume and adding 1% by volume acetic acid (Sigma-Aldrich, St. Louis, Mo., USA). Filtering capacity of filter plate 40 was characterized by infusing and electrospraying (i.e., using an ESI/ion funnel source 25) the solvent mixture and acquiring mass spectra with the instrument described in Example 1. By observing the m/z cut-off at which chemical noise in the acquired mass spectra was eliminated, cut-off threshold could be ascertained as a function of voltage applied to filter plate 40. Filter plate 40 voltages were adjusted in one-volt increments in the range from about 12 V to about 18 V.

Figure 4A:
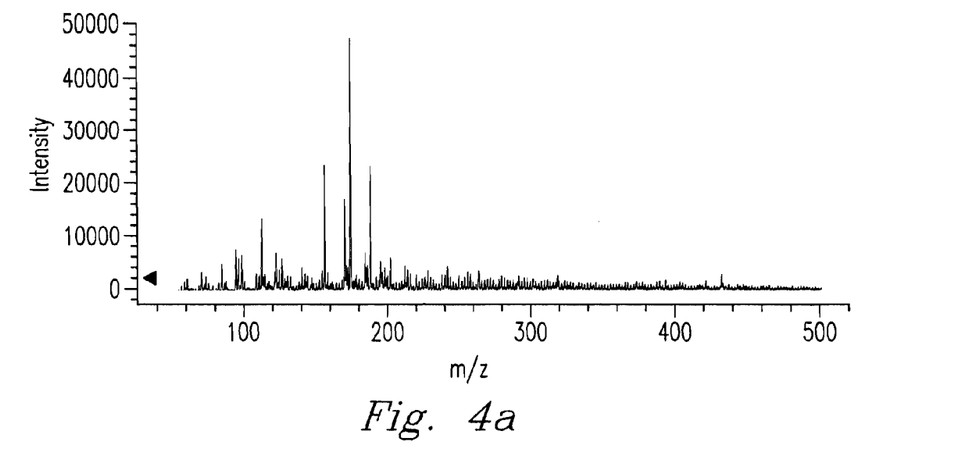
FIGS. 4a-4b present mass spectra of a solvent solution taken without and with low-mass filtering, respectively, filtering being done at an applied voltage of from about 12 V to about 18 V providing low-mass (m/z) cut-off at below about 200.
Figure 4B:
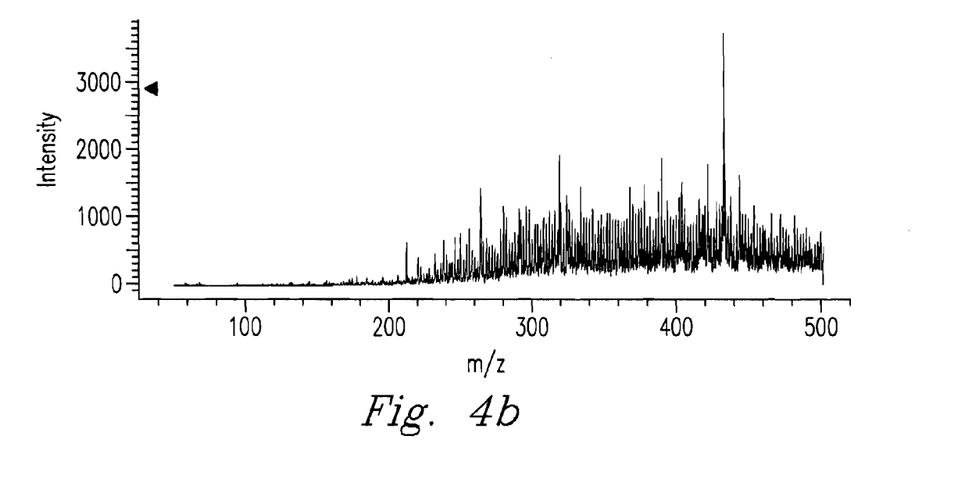
Figure 4C:
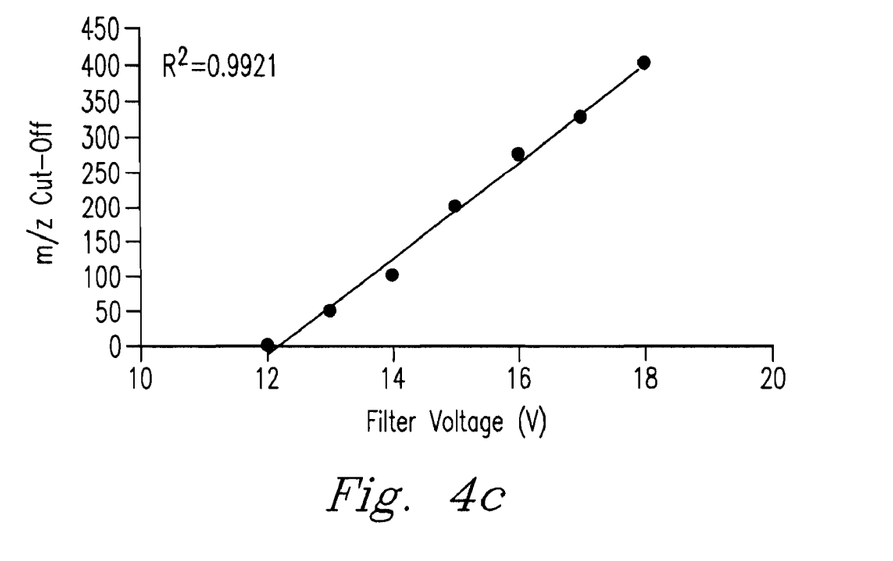
FIG. 4c is a plot relating (m/z) cut-off (mass filtering) of the filter plate as a function of voltage applied to the filter plate.

FIG. 4a presents a mass spectrum acquired from mass analysis of the solvent solution taken without use of filter plate 40 and associated low-mass filtering. Spectral peaks correspond to solvent clusters and impurities. FIG. 4b is a mass spectrum of the same solvent solution taken in conjunction with filter plate 40 at an applied voltage sufficient to provide for low-mass filtering. As shown by intensity scales in FIG. 4b, when voltage was applied to filter plate 40, noise in the low-mass region was virtually eliminated. Cut-off value (m/z) corresponding to a particular filter voltage was determined by observing where a large drop-off of any displayed chemical noise occurred. Drop off in noise observed in FIG. 4a (without filtering) occurred in FIG. 4b at an m/z value of about 200.

FIG. 4c shows a plot relating m/z cut-off values to applied filter voltages over the range from about 12 V to about 18 V. Results show the data to be substantially linear. In short, the effect of energy barrier potential to the upper limit of mass filter 40 is substantially linear.

Results provide an easy and useful method for calculating the voltage required to provide any desired m/z filtering in conjunction with filter plate 40. The ability to dynamically adjust potentials applied to filter 40 thereby achieving a desired mass filter range allows for quick adjustments to the analysis instrument based upon the sample properties, making the method available for dynamic low-m/z filtering in an automated process. Results further show that a simple low-mass filter can be created by adding a potential energy barrier at the exit aperture 65 of ion funnel 10.

Example 3

Example 3 describes the distribution of DC voltages and electric fields generated in the region near exit aperture 65 of filter plate 40 at an applied voltage of 15 V to filter plate 40. The DC electric field E was estimated using calculations based on the geometry shown in FIG. 1. As illustrated, e.g., in FIG. 2a, filter plate 40 can be considered a 3-dimensional plate having left and right surface planes (surfaces) 40-L and 40-R, respectively, and any suitable thickness (e.g., 0.5 mm), the left surface plane 40-L facing into the interior of ion funnel 10.

Figure 5A:
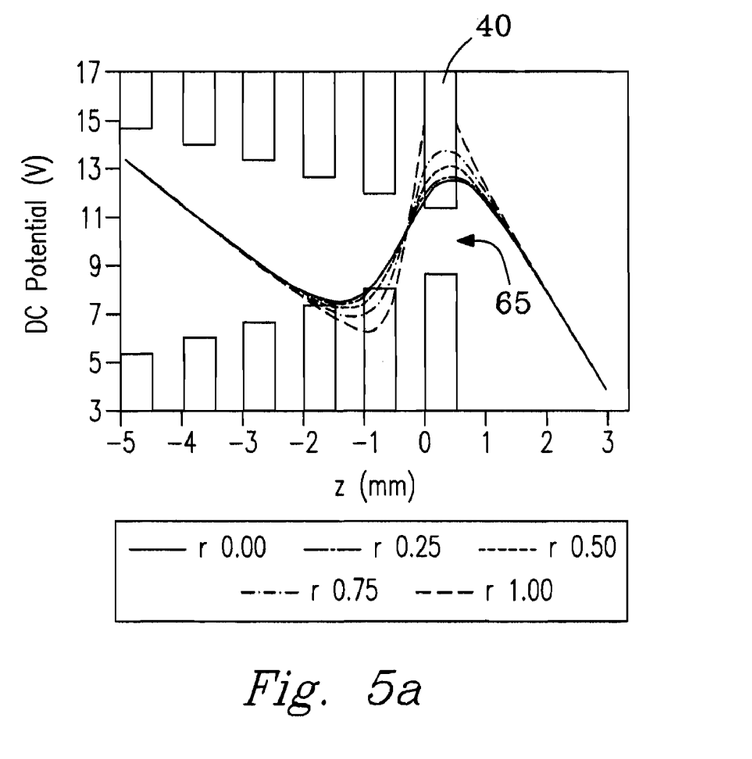
FIG. 5a is a plot of the calculated DC potential for a filtering plate voltage of 15 V as a function of distance along the ion funnel z axis with radial off-axis displacements "r" in the region near the filter plate.

FIG. 5a shows the distribution of DC potentials observed for radial distances (r) of 0, 0.25, 0.5, 0.75 and 1 mm, respectively from the center of exit aperture 65 of filter plate 40 toward the radial edge of aperture 65 of filtering plate 40 as a function of axial coordinate "z" for rear section 45 of funnel 10. The origin of axial coordinate "z" is positioned at leftmost surface plane 40-L (left surface) of filter plate 40. Small variations in DC potential are observed as a function of distance from the center of aperture 65, with slight increases in potential observed at positive displacements up to about 1 mm from the center of aperture 65. At an applied potential of 15 V, for example, results show a DC potential of from about 13 V to about 15 V at aperture 65, with a potential difference or spread of about 2 V.

Figure 5B:
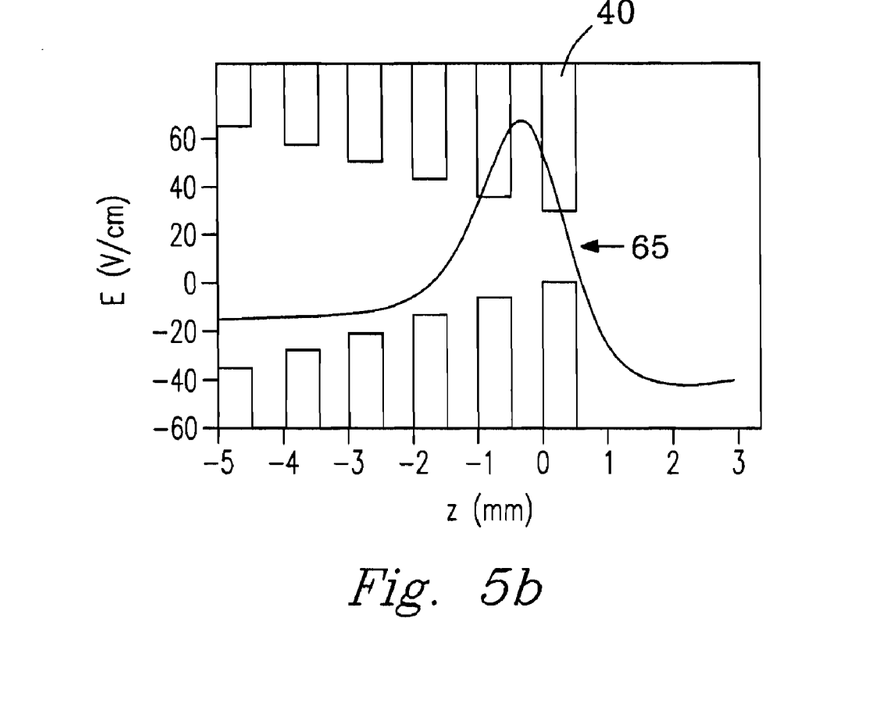
FIG. 5b is a plot of the axial electric field strength (E) for a filtering plate voltage of 15 V as a function of distance along the ion funnel z axis in the region near the filter plate.
Figure 5C:
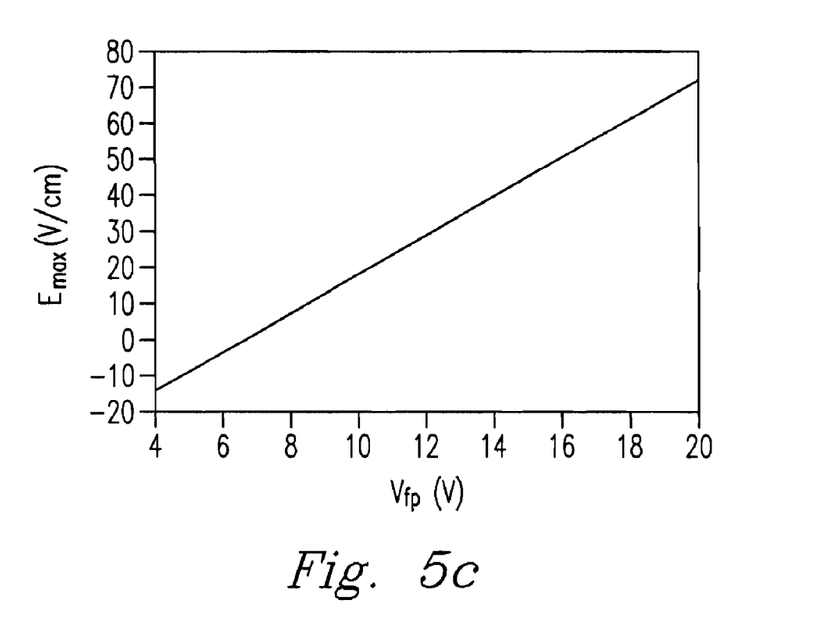
FIG. 5c is a plot of the electric field maximum (E) calculated as a function of voltage ($V_{fp}$) applied to the filter plate.

FIG. 5b shows the electric field E (V/cm) strength associated with the applied barrier potential, calculated as the derivative of the potential over the axial displacement z. Data show a peak field E with a slight negative axial displacement, indicating the actual placement of the potential barrier exerted near exit aperture 65 of plate 40 where low m/z ions are filtered. FIG. 5c shows the maximum axial electric field ($E_{max}$) as a function of applied filter plate voltage ($V_{fp}$). The electric field maximum is demonstrated to be a linear function of the voltage applied to filter plate 40. For example, an applied filter voltage of 15 V results in an electric field of about $E_{max}$=45 V/cm. According to experimental data discussed previously in reference to FIG. 4c, a DC offset of 15 V at filter plate 40 corresponds to a low mass cut off at about m/z 200. The mobility coefficient K, estimated using equation [1] through [2], is then determined to be K=0.07 m²/V s, typical for conditions of 2 Torr $N_2$ buffer gas. Substituting the estimated mobility value of 0.07 m²/V s into equation [2], a cross section σ=120 Å² is obtained which agrees with those reported for ions of similar m/z. In the instant case, the effective upper limit of low-mass filtering provided by filter plate 40 is an m/z of about 500. At filter voltages that produce a cut-off greater then ~m/z 500, some attenuation of higher-m/z species is observed. High m/z ions experience reduced RF focusing and are ejected in the radial direction when potential of filter plate 40 is increased above 20 V, corroborating observations of low-mass filtering below about m/z less than or equal to about 500 obtained experimentally. The effective cut-off limit can be increased by increasing RF voltage (the effective potential) of ion funnel 10 which decreases the attenuation. However, overall transmission efficiency of funnel 10 may be reduced in some cases as a consequence. Example 4 presents an example of this phenomenon, shown for analysis of a polyethylene glycol solution.

Example 4

Example 4 describes attenuation effects observed in mass spectra of higher-massed peaks above an m/z of 500 with and without use of filter plate 40.

A polyethylene glycol (M.W.=1450) stock solution was prepared by dissolving ~15 mg PEG (Sigma-Aldrich, St. Louis, Mo., USA) and ~15 mg ammonium acetate (Fisher Scientific, Hampton, N.H., USA) into 10 mL of 50:50 acetonitrile/water and 0.2% by volume formic acid (Sigma-Aldrich, St. Louis, Mo., USA). A PEG solution for ESI infusion was then prepared from the stock by performing a 100× dilution in 0.02M ammonium acetate in 50:50 acetonitrile/water and 0.2% formic acid. Mass spectra were acquired for the diluted PEG solution using the ESI/ion funnel source described in Example 1.

Figure 6A:
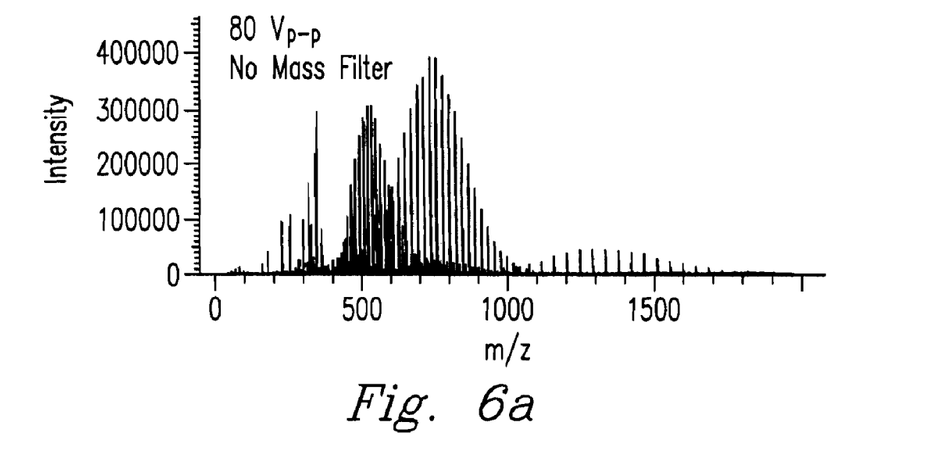
FIG. 6a is a mass spectrum of a polyethylene glycol solution taken at an RF voltage of 80 $V_{p-p}$ (peak-to-peak) without use of the mass filter plate.
Figure 6B:
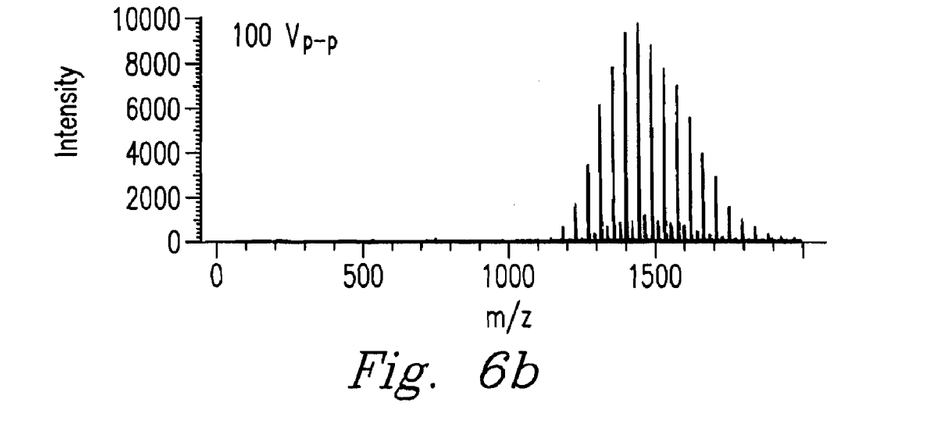
FIGS. 6b-6f are mass spectra of a polyethylene glycol solution taken at RF voltages (peak-to-peak) of 100 $V_{p-p}$ (FIG. 6b), 90 $V_{p-p}$ (FIG. 6c), 80 $V_{p-p}$ (FIG. 6d), 70 $V_{p-p}$ (FIG. 6e), and 60 $V_{p-p}$ (FIG. 6f) using a filter plate at a mass filter voltage of 24.0 V and a mass (m/z) filter cut-off of m/z=1100.
Figure 6C:
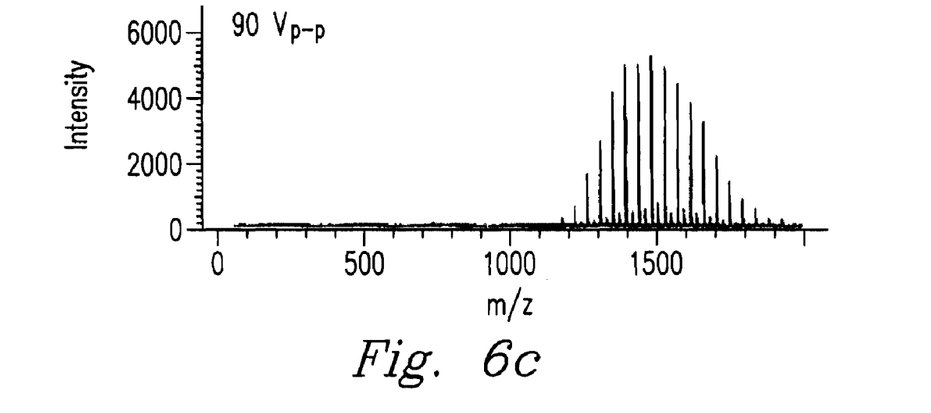
Figure 6D:
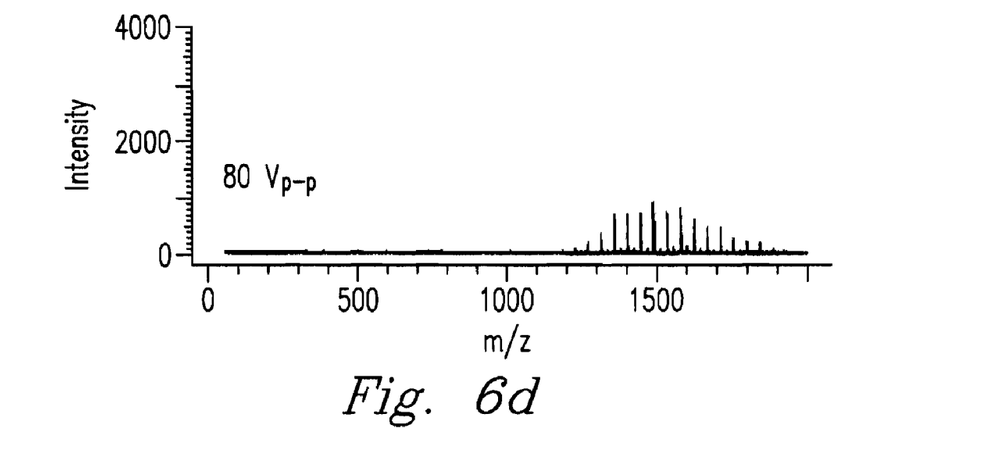
Figure 6E:
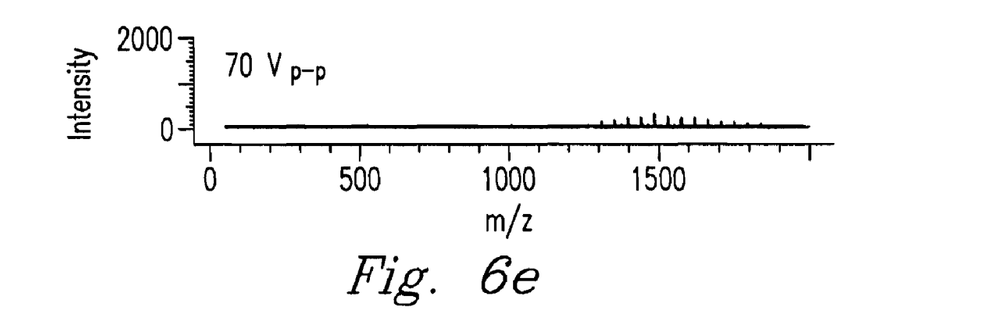
Figure 6F:
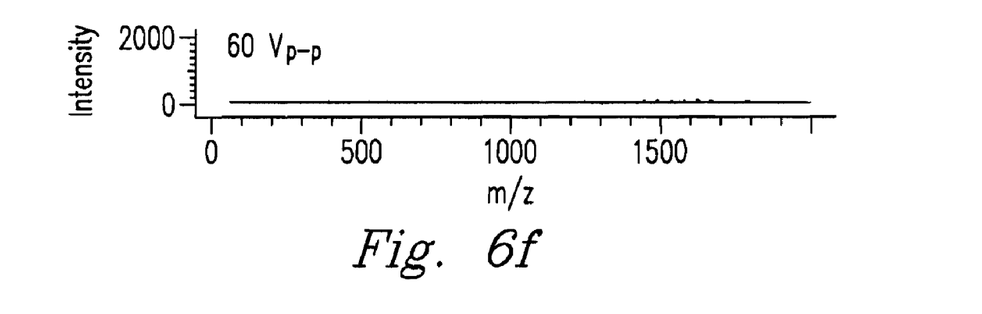

FIG. 6a shows a mass spectrum obtained from analysis of the PEG solution at an RF peak-to-peak voltage of 80 ($V_{p-p}$) without use of mass filtering. Peaks spanning the entire mass window were detected. FIGS. 6b-6f show spectra from analysis of the PEG solution acquired in conjunction with use of filter plate 40 at an applied voltage of 24.0 V and a mass filter cut-off of m/z 1100. Spectra were acquired by incrementally reducing RF peak-to-peak voltage ($V_{p-p}$) over the range from about 100 $V_{p-p}$ (FIG. 6b) to 60 $V_{p-p}$ (FIG. 6f) in 10 V decrements. FIGS. 6b-6e show gradually increasing peak attenuation with each decrement in voltage. In FIG. 6f, at 60 $V_{p-p}$, attenuation is sufficiently large to effectively prohibit detection of any PEG peaks. Increasing RF voltage results in an increased effective potential in ion funnel 10 that greatly reduces attenuation by prohibiting radial ion loss in the mass filtering region of ion funnel 10.

Example 5

Example 5 details use and evaluation of low-mass filtering in conjunction with use of filter plate 40 for a liquid chromatography-mass spectrometry (LC-MS) analysis of a Bovine Serum Albumin (BSA) tryptic digest.

A tryptic digest of BSA (Sigma-Aldrich, St. Louis, Mo., USA) was made by denaturing the BSA protein in urea and thiourea, and reducing it with dithiothreitol followed by a 10× dilution in 100 mM ammonium bicarbonate. Digestion was then performed with trypsin (Promega, Madison, Wis., USA) in a 1:50 ratio of enzyme to protein. The digest was cleaned using a $C_{18}$ SPE column from Supelco (Bellefonte, Pa., USA) and then concentrated down to 0.1 mg/mL.

The ESI/ion funnel configuration described in Example 1 and in reference to FIG. 2b was employed. Mesh plate 42 was biased with a DC power supply 63 used to float the ground of picoammeter 64 (Keithley Model 6485, Cleveland, Ohio, USA). Picoammeter 64 was used to detect ion current impacting mesh 44 and plate 42. The LC-MS analyses of the BSA tryptic digest were performed using an Agilent 1100 series capillary LC system. Samples were analyzed by loading 800 ng of a BSA tryptic digest solution onto a 150 μm i.d.×25 cm long reverse-phase packed capillary column with 5-μm diameter $C_{18}$ particles (Jupiter, Phenomenex, Schlieren, Switzerland). Samples were separated at a constant flow rate of 2 μL/min and a linear gradient was used to elute the peptides, using 0.2% acetic acid and 0.05% TFA in water (solvent A) and 90% acetonitrile with 0.1% TFA (solvent B).

Ion current measurements were collected by biasing mesh plate 42 in ion funnel 10 to −10 V and detecting ion current values with picoammeter 64. In order to record ion current during the LC-MS experiments, in-house developed software was used to receive and store the current measurements from picoammeter 64 in one second intervals.

The BSA tryptic digest was separated via capillary LC and analyzed with a single quadrupole mass spectrometer, as described in Example 1, with and without mass filtering. In order to provide a control data set, filter 40 was initially set at +5 V which did not create a potential energy barrier and did not block any low-mass ions and detecting the resulting ion current once every second with picoammeter 64, FIG. 7a. Space charge related to low-mass ("background") species during the LC-MS analysis of the protein digest was detected, and the ability of mass filter 40 to block this background space charge was tested under the same conditions as the control LC-MS experiment except with filter plate 40 biased to a voltage which produced a mass filter 40 with a cut-off at m/z 200 and detecting the resulting ion current once every second with picoammeter 64, FIG. 7b.

Figure 7A:
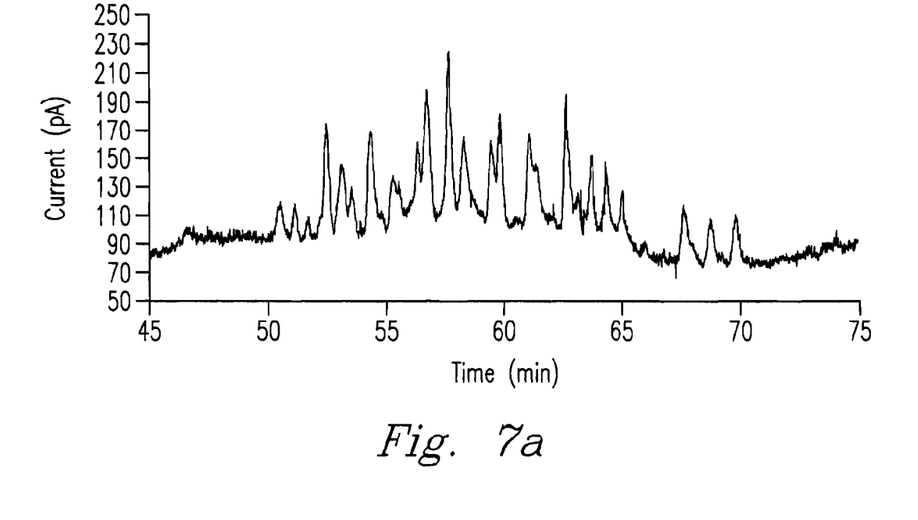
FIGS. 7a-7b present ion-current chromatograms from LC-MS analyses of a Bovine Serum Albumin (BSA) tryptic digest solution without and with use of a mass filter plate.
Figure 7B:
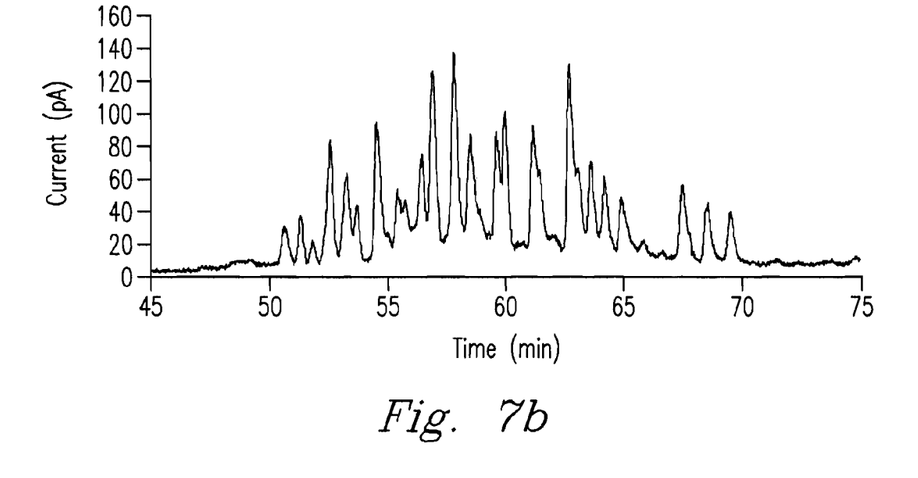

During LC-MS analysis, a large portion of total ion current exiting ESI source 25 was from unwanted, background species, which unnecessarily increased the space charge in the mass spectrometer. As shown in FIG. 7a, without use of filter 40 and associated filtering, ion current measured during peptide elution ranged from about 130 to 230 pA. The ion current background was about 90 pA, representing from 40 to 70% of the total current. In FIG. 7b, use of filter 40 and associated filtering during peptide elution resulted in an ion current of from 40 to 140 pA, with a contribution from background species of about 5 pA, a drop of from 40% to 70% to about 4% to 13% of the total ion current. Use of filter plate 40 and low-mass filtering assured that a large majority of ions entering the mass spectrometer from the ESI source were actual tryptic peptides and not unwanted background species that would unnecessarily add to space charge.

In sum, a significant portion of ions exiting funnel 10 are of no interest. Use of filter plate 40 removes low-mass background species, lowering space-charge effects which can hamper the ability of MS to perform. Space-charge shields the potentials the MS uses. Removal of space-charge effects by use of filter plate 40 (either with pre-analysis or real-time adjustments) thus improves instrument performance, and is applicable to any mass spectrometer that employs ion trapping for accumulation, storage, and/or m/z analysis.

We claim:

1. A method for selectively filtering ions having a low mass to charge ratio from a current of flowing ions in an ionization electrospray, said method comprising the steps of:
generating an independent electric field having a preselected voltage at an exit end of an electrodynamic ion funnel; and
flowing an ion stream comprising ions having a variety of drift velocities defined by their individual ion mobility therein in a carrier gas at a preselected carrier gas velocity through said electric field; whereby ions having a drift velocity greater than and opposite to said preselected carrier gas velocity are removed from said ion stream and ions having a drift velocity less than, and in the same direction as, said carrier gas are left within said ion stream.

2. The method of claim 1, wherein said preselected voltage is a preselected DC voltage.

3. The method of claim 1, wherein ions removed from said ion stream have a mass cut-off value in the range from about 50 m/z to about 500 m/z.

4. The method of claim 1, wherein said independent electric field is configured to remove ions having a preselected mass cut-off value above an m/z of about 500 and a voltage gain that compensates for signal attenuation.

5. The method of claim 1, further comprising the step of directing said continuously flowing ion stream into a device for performing gas-phase ion separation and analysis selected from the group consisting of ion mobility spectrometry (IMS), field asymmetric waveform ion mobility spectrometry (FAIMS), mass spectrometry (MS), tandem MS, multiple MS stages of any kind, gas chromatography (GC), LC-MS, photoelectron spectroscopy, photodissociation spectroscopy, and combinations thereof.

6. The method of claim 1, further comprising the step of directing said continuously flowing ion stream into a device coupled on-line or off-line that performs at least one method for separations and analysis of substances in solid or liquid phases selected from the group consisting of liquid chromatography (LC), normal phase LC, reversed phase LC, strong-cation exchange LC, supercritical fluid chromatography, capillary electrophoresis, capillary isoelectric focusing, gel separations in one or more dimensions, SDS-PAGE, 2-D gel, and combinations thereof.

7. The method of claim 1, wherein said flowing ion stream includes ions that are macro-molecular ions selected from the group consisting of proteins, protein complexes, peptides, polypeptides, oligonucleotides, DNA, RNA, polymers, oligosaccharides, dendrimers, fragments thereof, and combinations thereof.

8. The method of claim 1, wherein said electric field is generated by applying said voltage to an electrode of said electrodynamic ion funnel.

9. The method of claim 8, wherein said ion funnel includes a carrier gas pressure in the range from about 1 Torr to about 10 Torr.

10. The method of claim 8, wherein said ion funnel includes a carrier gas pressure in the range from about 1 Torr to about 3 Torr.

11. The method of claim 2, wherein said preselected voltage is a positive voltage for positively charged ions in said ion stream or a negative voltage for negatively charged ions in said ion stream.

12. The method of claim 2, wherein said electric field is dynamically adjusted in real time to remove ions selectively from said continuous ion stream.

13. The method of claim 12, wherein said electrical field is adjusted by selection of voltages that produce an electric field in the range from about 0 V/cm to about 100 V/cm or greater, selected as a function of the velocity of said carrier gas.

14. A method for reducing space charge effects in an analytical electrospray system said method characterized by the step of:
continuously flowing an ion stream having ions with differing ion mobilities suspended in a carrier gas through an independent electric field positioned at the exit end of an electrodynamic ion funnel whereby ions having a drift velocity greater than and opposite to the preselected carrier gas velocity are removed from said ion stream and ions having a drift velocity less than and in same direction as the carrier gas are left within said ion stream.

15. The method of claim 14, wherein said preselected voltage is dynamically adjusted in real time to selectively filter said portion of said ions from said continuously flowing ion stream.

* * * * *

UNITED STATES PATENT AND TRADEMARK OFFICE
CERTIFICATE OF CORRECTION

| | | |
|---|---|---|
| PATENT NO. | : 7,514,676 B1 | Page 1 of 1 |
| APPLICATION NO. | : 11/251529 | |
| DATED | : April 7, 2009 | |
| INVENTOR(S) | : J S Page, K Tang and R D Smith | |

It is certified that error appears in the above-identified patent and that said Letters Patent is hereby corrected as shown below:

Column 1, lines 4 through 7 of the issued patent should read as follows:

The invention was made with Government support under grant number RR018522 from the U.S. National Institutes of Health and contract DE-AC05-76RL01830 awarded by the US Department of Energy. The government has certain rights in the invention.

Signed and Sealed this
Eleventh Day of September, 2012

David J. Kappos
*Director of the United States Patent and Trademark Office*